US009377423B2

(12) United States Patent  
Hirschfeld et al.

(10) Patent No.: US 9,377,423 B2  
(45) Date of Patent: Jun. 28, 2016

(54) SYSTEMS AND METHODS FOR HANDLING SUBSTRATES AT BELOW DEW POINT TEMPERATURES

(71) Applicant: Cascade Microtech, Inc., Beaverton, OR (US)

(72) Inventors: Botho Hirschfeld, Dresden (DE); Axel Becker, Dresden (DE)

(73) Assignee: Cascade Microtech, Inc., Beaverton, OR (US)

( * ) Notice: Subject to any disclaimer, the term of this patent is extended or adjusted under 35 U.S.C. 154(b) by 306 days.

(21) Appl. No.: 14/141,781

(22) Filed: Dec. 27, 2013

(65) Prior Publication Data

US 2014/0185649 A1     Jul. 3, 2014

Related U.S. Application Data

(60) Provisional application No. 61/747,686, filed on Dec. 31, 2012.

(51) Int. Cl.
*G01N 25/66*     (2006.01)
*G01R 31/00*     (2006.01)
*G01R 31/28*     (2006.01)

(52) U.S. Cl.
CPC .............. *G01N 25/66* (2013.01); *G01R 31/00* (2013.01); *G01R 31/2862* (2013.01)

(58) Field of Classification Search
CPC .................................................. G01N 25/68
USPC .............................................................. 374/28
See application file for complete search history.

(56) References Cited

U.S. PATENT DOCUMENTS

| 4,693,211 A | 9/1987 | Ogami et al. |
| 4,817,299 A | 4/1989 | Pabst |
| 5,369,891 A | 12/1994 | Kamikawa |
| 5,657,553 A | 8/1997 | Tarui et al. |
| 5,885,353 A | 3/1999 | Strodtbeck et al. |
| 6,099,643 A | 8/2000 | Ohtani et al. |

(Continued)

FOREIGN PATENT DOCUMENTS

| EP | 0511928 | 3/1996 |
| JP | 2000-310459 | 11/2000 |

OTHER PUBLICATIONS

English-language translation of Japanese Patent Publication No. 2000-310459, Nov. 7, 2000.

*Primary Examiner* — Lisa Caputo  
*Assistant Examiner* — Tran M Tran  
(74) *Attorney, Agent, or Firm* — Dascenzo Intellectual Property Law, P.C.

(57) ABSTRACT

Disclosed systems and methods for testing a device under test (DUT) with a probe system are selected to test a DUT at a temperature below the dew point of the ambient environment surrounding the probe system. Probe systems include a measurement chamber configured to isolate a cool, dry testing environment and a measurement chamber door configured to selectively isolate the internal volume of the measurement chamber. When a DUT, that is or is included on a substrate, is tested at a low temperature, systems and methods are selected to heat the substrate in a dry environment, at least partially isolated from the measurement chamber, to at least a temperature above the dew point and/or the frost point of the ambient environment.

23 Claims, 3 Drawing Sheets

(56) References Cited

U.S. PATENT DOCUMENTS

| | | |
|---|---|---|
| 6,263,587 B1 | 7/2001 | Raaijmakers et al. |
| 6,473,993 B1 | 11/2002 | Yagi et al. |
| 7,900,373 B2 * | 3/2011 | Reitinger .......... H01L 21/67109 |
| | | 118/712 |
| 8,343,280 B2 * | 1/2013 | Iimuro .............. H01L 21/67248 |
| | | 118/724 |
| 8,525,539 B2 * | 9/2013 | Washio .............. G01R 31/2887 |
| | | 324/756.01 |
| 2002/0135389 A1 | 9/2002 | Melgaard et al. |
| 2007/0235134 A1 | 10/2007 | Iimuro |
| 2011/0291022 A1 | 12/2011 | Lee et al. |
| 2011/0291030 A1 | 12/2011 | Lee |
| 2013/0077651 A1 * | 3/2013 | Lee ................... H01L 21/67253 |
| | | 374/28 |

\* cited by examiner

SYSTEMS AND METHODS FOR HANDLING SUBSTRATES AT BELOW DEW POINT TEMPERATURES

RELATED APPLICATION

This application claims priority under 35 U.S.C. §119(e) to U.S. Provisional Patent Application No. 61/747,686, which was filed Dec. 31, 2012, and the complete disclosure of which is incorporated herein by reference for all purposes.

FIELD OF THE DISCLOSURE

The present disclosure is directed generally to systems and methods for handling substrates at below dew point temperatures.

BACKGROUND OF THE DISCLOSURE

It may be desirable to test a device under test (DUT) contained on a substrate at one or more test temperatures. These test temperatures may include a temperature below a dew point temperature of air in an ambient environment that surrounds a test system that is utilized to perform the test. Under these conditions, water may condense on the substrate (and the DUT) if the substrate is exposed to the ambient environment while the substrate is at test temperature. For certain substrates and/or under certain conditions, it may be desirable to minimize, or even prevent, this condensation.

A DUT may be tested in a measurement chamber at low temperatures, such as at temperatures below the ambient environment dew point temperature. Measurement chambers may be fluidically and thermally isolated from the ambient environment while the DUT is being tested. However, insertion and removal of substrates may require gaseous and thermal contact between the ambient environment and the measurement chamber (as well as the substrate). Hence, a measurement chamber may need active cooling to maintain a low test temperature. Once tested, a substrate may be at a low test temperature. To avoid condensation on the DUT and/or the substrate when exposed to the ambient environment, the substrate may be heated to ambient temperature in the measurement chamber (consequently heating at least a portion of the measurement chamber). Once the potential for condensation is reduced or eliminated, the substrate may be removed from the measurement chamber. To use the measurement chamber again, with the original or a subsequent substrate, the measurement chamber then needs to be cooled to return to the test temperature. Such heating and cooling cycles may limit the availability of the measurement chamber for testing, may cause wear on measurement chamber components, and/or may limit the total throughput of tested substrates. Thus, there exists a need for improved systems and methods for handling substrates at below dew point temperatures.

SUMMARY OF THE DISCLOSURE

Disclosed systems and methods for testing a device under test (DUT) with a probe system are selected to test a DUT at a temperature below the dew point of the ambient environment surrounding the probe system. Devices under test (DUTs) may be, and may be included on, a substrate such as a semiconductor wafer.

Probe systems may comprise: (i) a measurement chamber that defines a measurement chamber internal volume, (ii) a measurement chamber temperature-control assembly that is configured to cool a substrate within the measurement chamber internal volume to a temperature below a dew point temperature and/or a frost point temperature of an ambient environment surrounding the probe system, (iii) an access chamber that defines an access chamber internal volume, (iv) a measurement chamber door that is configured to selectively isolate the measurement chamber internal volume from the access chamber internal volume, (v) a transfer assembly that is configured to selectively transfer a substrate through the measurement chamber door and thus between the measurement chamber internal volume and the access chamber internal volume, and (vi) an access chamber purging assembly that is configured to selectively direct a first dry gas stream in fluid contact with the substrate when the substrate is located within the access chamber internal volume.

Methods for testing a DUT with a probe system including a measurement chamber may comprise: (i) establishing a low temperature and a dry environment within a measurement chamber internal volume of the measurement chamber, (ii) placing a substrate with a DUT into the measurement chamber internal volume, (iii) testing the DUT, (iv) removing the substrate from the measurement chamber internal volume, and (v) dry heating the substrate at least partially outside of the measurement chamber internal volume. Methods further may comprise repeating the placing, the testing, the removing, and/or the dry heating under different conditions and/or with different substrates.

DETAILED DESCRIPTION OF THE DISCLOSURE

Figure 1:
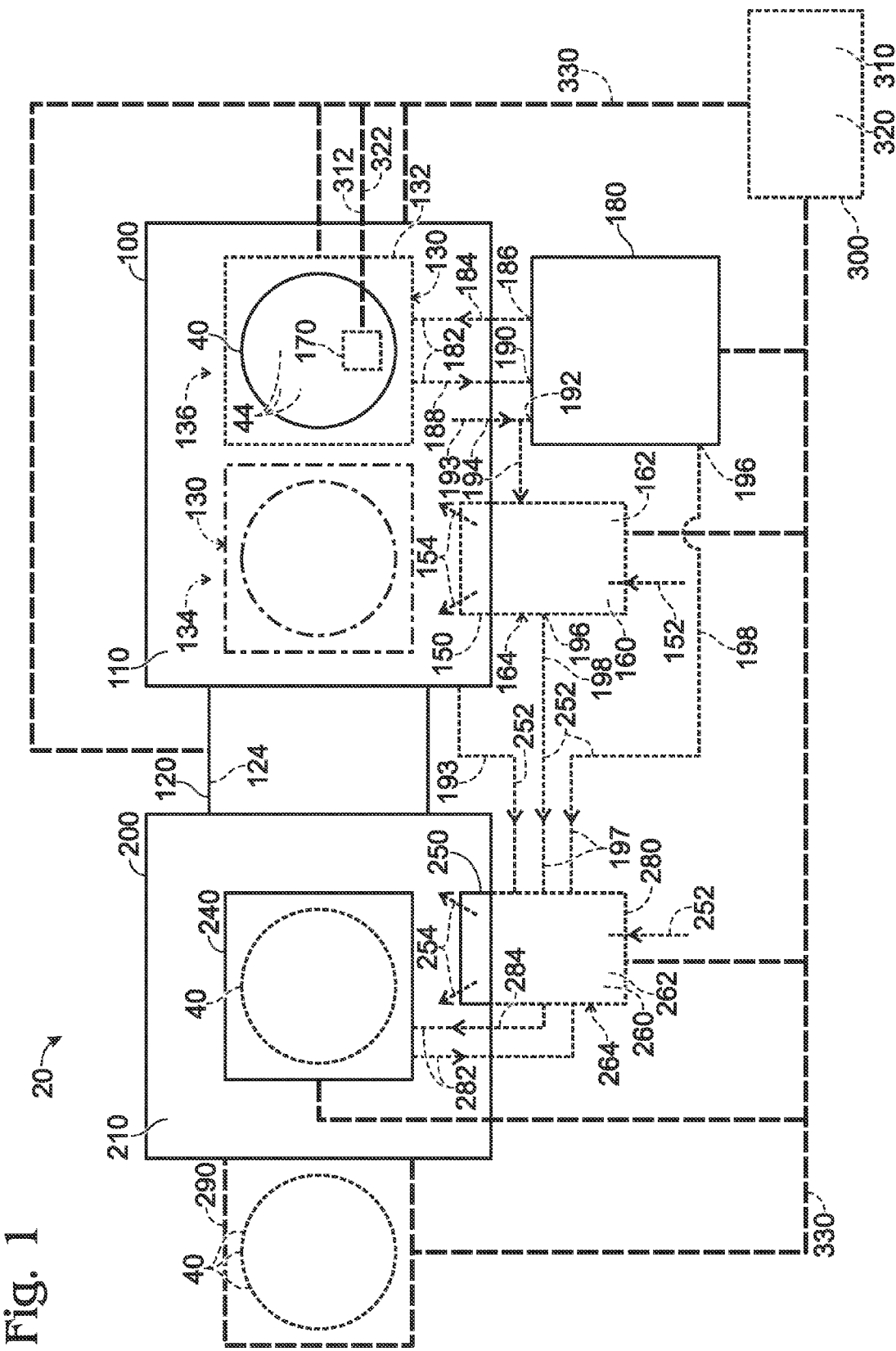
FIG. 1 is a schematic representation of probe systems that may be utilized with and/or include the systems and methods according to the present disclosure.

FIGS. 1-4 illustrate various probe systems 20, including components thereof, and methods 400 for testing a device under test with probe systems 20. Elements that serve a similar, or at least substantially similar, purpose are labeled with numbers consistent among the figures. Like numbers in each of FIGS. 1-4, and the corresponding elements, may not be discussed in detail herein with reference to each of FIGS. 1-4. Similarly, all elements may not be labeled in each of FIGS. 1-4, but reference numerals associated therewith may be used for consistency. Elements, components, steps, and/or features that are discussed with reference to one or more of FIGS. 1-4 may be included in and/or used with any of FIGS. 1-4 without departing from the scope of the present disclosure. In general, elements that are likely to be included are illustrated in solid lines, while elements that may be optional or alternatives are illustrated in dashed lines. However, elements that are shown in solid lines are not necessarily essential, and an element shown in solid lines may be omitted without departing from the scope of the present disclosure.

As illustrated in FIG. 1, probe systems 20 include a measurement chamber 100 that defines a measurement chamber internal volume 110. The measurement chamber is generally an enclosed compartment of the probe system. Probe systems 20 may include an access chamber 200 that defines an access chamber internal volume 210. The access chamber 200 may be an enclosed or an open compartment of the probe system. A measurement chamber door 120 is located between the measurement chamber 100 and the access chamber 200 and is configured to selectively isolate (e.g., fluidically and/or thermally isolate) the measurement chamber internal volume 110 from the access chamber internal volume 210. Where the access chamber is an at least partially open compartment, the access chamber internal volume may be a volume outside of the measurement chamber internal volume and in proximity to the measurement chamber door.

Generally, probe systems 20 are configured to test a substrate 40, optionally a plurality of substrates 40, at below the dew point temperature and/or the frost point temperature of the ambient environment surrounding the probe system. Probe systems 20 may be configured to test the substrate at elevated temperatures (higher than the dew point temperature and/or the frost point temperature of the ambient environment). Probe systems 20 are configured to cool the substrate to, and/or maintain the substrate at, a low temperature (lower than the dew point temperature and/or the frost point temperature of the ambient environment) in a dry environment (where the dew point temperature and/or the frost point temperature is lower than the local temperature). Probe systems 20 are configured to test the substrate at the low temperature in the measurement chamber internal volume 110. At least a portion of the measurement chamber may be maintained at a similarly low temperature.

When testing at the low temperature is complete, the probe systems 20 are configured to heat, in a dry environment, the substrate 40 from the low temperature to a temperature above the dew point temperature and/or frost point temperature of the ambient environment. Generally, probe systems 20 are configured to heat the substrate within the access chamber internal volume 210 and/or to heat without substantially affecting the temperature of the measurement chamber internal volume 110.

Probe systems 20 include an access chamber purging assembly 250 that is configured to direct an access chamber dry gas stream 254 to establish and/or maintain the substrate in a dry environment. For example, the access chamber purging assembly 250 may direct the access chamber dry gas stream 254 toward, to, proximate, into fluid communication with, and/or into contact with the substrate 40. The access chamber dry gas stream 254, which may be heated, also may be referred to herein simply as a dry gas stream 254. The dry gas stream 254 also may heat the substrate, e.g., when the dry gas stream is heated (having a temperature greater than the substrate). The dry gas stream 254 may be sourced from an access chamber source gas stream 252. As an illustrative, non-exclusive example, the dry gas stream 254 may be sourced or otherwise obtained from the dry environment of the measurement chamber. The access chamber source gas stream may be heated by an optional measurement chamber gas conditioner 164 (which also may control the temperature and/or humidity of gas supplied to the measurement chamber 100), a measurement chamber temperature-control assembly 180 (which also may control the temperature of the measurement chamber and/or components thereof), an optional access chamber gas conditioner 264 (which may control the temperature and/or humidity of gas supplied to the access chamber 200), and/or an optional access chamber temperature-control assembly 280 (which may control the temperature of the access chamber and/or components thereof). As used herein, controlling a property, such as temperature or pressure, may include increasing the property; decreasing the property; maintaining the property at, above, or below a threshold, or selected, value; maintaining the property within or outside of a threshold, or selected, range of values; adjusting the property; and/or regulating the property.

As discussed, the measurement chamber door 120 of a probe system 20 is configured to selectively isolate the measurement chamber internal volume 110 from the access chamber internal volume 210. Generally, the measurement chamber door 120 has an open state, in which the measurement chamber door is configured to allow physical transport between the measurement chamber internal volume and the access chamber internal volume, and a closed state, in which the measurement chamber door is configured to isolate, fluidically and/or thermally, the measurement chamber internal volume and the access chamber internal volume. Further, the closed state may be configured to restrict transport between the measurement chamber and the access chamber. The measurement chamber door may be configured to selectively transition between the open state and the closed state. In the open state, the measurement chamber door may provide fluid communication between the measurement chamber internal volume and the access chamber internal volume and/or may permit a transfer assembly 240 to convey the substrate 40 therethrough. In the closed state, the measurement chamber door may restrict the transfer assembly from conveying the substrate therethrough. The measurement chamber door may be a suitable structure that at least partially spans a measurement chamber doorway 124 between the measurement chamber and the access chamber. The measurement chamber door may include, and optionally may be, a gas curtain, in which case the measurement chamber door may be in the closed state and the open state simultaneously (e.g., the gas curtain may allow physical transport through the measurement chamber doorway while fluidically isolating the measurement chamber internal volume from the access chamber internal volume).

Probe systems 20 may include two or more measurement chamber doors 120, with each independently configured to allow physical transport to, from, and/or between the measurement chamber internal volume 110 and the access chamber internal volume 210. For example, one measurement chamber door may be configured to selectively permit ingress of one substrate into the measurement chamber internal volume, and another measurement chamber door may be configured to selectively permit egress of another substrate out of the measurement chamber internal volume.

Probe systems 20 may include a chuck 130, which may be temperature controlled, located within the measurement chamber internal volume 110. The chuck is configured to support the substrate 40, which may include and/or be a device under test (DUT) 44 (typically a plurality of devices under test (DUTs) 44). The chuck may include and/or be in mechanical communication with a chuck translation assembly 132. The chuck translation assembly may be configured to locate, translate, rotate, and/or move the chuck within the measurement chamber internal volume 110 and/or to move the chuck relative to a probe assembly 170 and/or the measurement chamber 100. The chuck may move, and/or be controlled to move, relative to the probe assembly to bring one or more probe tips of the probe assembly into contact with the DUT and/or to separate the one or more probe tips from the DUT. In addition, probe systems may include the transfer assembly 240, which is configured to selectively transfer the substrate through the measurement chamber door 120 and/or between the measurement chamber internal volume 110 and the access chamber internal volume 210. Chuck 130 may define at least a load position 134, in which the chuck is located to receive substrate 40 from outside the measurement chamber (e.g., from the transfer assembly), and a test position 136, in which the chuck is located for testing and/or contact with the probe assembly.

DUTs 44 may include any suitable structure that is configured to be contacted by, electrically contacted by, mechanically contacted by, optically contacted by, and/or tested by probe system 20. For clarity, electrical contact includes contact via electrical signals (which may include electromagnetic radiation). Optical contact includes optical access and/or contact via optical signals. As illustrative, non-exclusive examples, DUTs 44 may include and/or be any suitable integrated circuit, semiconductor device, electronic device, microelectronic mechanical system, optoelectronic device, and/or optical device. Similarly, substrate 40 may include any suitable structure that may include, contain, and/or have formed thereon DUTs 44. Substrates 40 generally are thin (e.g., having a thickness typically between 0.05 mm and 2 mm) and thermally conductive (e.g., having a thermal conductivity typically greater than 0.2 W/(m·K), commonly greater than 10 W/(m·K)). As illustrative, non-exclusive examples, substrate 40 may include and/or be any suitable wafer, chip, semiconductor wafer, semiconductor chip, silicon wafer, silicon chip, Group III-V semiconductor wafer, Group III-V semiconductor chip, and/or printed circuit.

Probe systems 20 may be configured to supply a measurement chamber dry gas stream 154 (also referred to herein as dry gas stream 154) to the measurement chamber 100. For example, probe system 20 may include the measurement chamber gas conditioner 164, which is configured to provide the dry gas stream 154 to a measurement chamber purging assembly 150. The measurement chamber gas conditioner may be configured to adjust and/or control the humidity and/or the temperature of a gas, transforming a measurement chamber source gas stream 152, which is supplied to the measurement chamber gas conditioner, into the measurement chamber dry gas stream 154, which is emitted by the measurement chamber gas conditioner. For example, the measurement chamber gas conditioner may include a dehumidifier 160 (configured to reduce and/or maintain gas humidity) and/or a gas heater/chiller 162 (configured to heat and/or chill a gas). The measurement chamber purging assembly may be located within and/or may be in fluid communication with the measurement chamber internal volume 110, and may direct the dry gas stream 154 into the measurement chamber internal volume and/or direct the dry gas stream 154 into fluid contact with the chuck 130 and/or the substrate 40 (when present on the chuck). The measurement chamber purging assembly may be configured to create a positive pressure differential between the measurement chamber internal volume and the ambient environment. The measurement chamber purging assembly may be configured to flow the dry gas stream 154 to essentially exclude gas from the ambient environment (e.g., configured as a gas curtain).

Probe systems 20 include the measurement chamber temperature-control assembly 180, which is configured to adjust and/or to control the temperature of the measurement chamber internal volume 110 and/or components therein. Generally, the measurement chamber temperature-control assembly is configured to cool the substrate 40, when present within the measurement chamber internal volume, to a temperature below a dew point temperature and/or a frost point temperature of the ambient environment surrounding the probe system. The measurement chamber temperature-control assembly also may be configured to heat the measurement chamber internal volume and/or components therein. Components within the measurement chamber internal volume may include the chuck 130, the substrate 40 (e.g., when present on the chuck), and/or the dry gas stream 154. For example, the measurement chamber temperature-control assembly may cool and/or heat the chuck by conduction, convection, and/or radiation. The measurement chamber temperature-control assembly may include at least one of a resistive heater, a thermoelectric device, a Peltier device, a heat pump, a vapor-compression device, a refrigerant, a circulating pump, a heat-transfer fluid, and a heat exchanger. As discussed, substrate 40 may be or include at least one DUT 44, and substrate 40 often may be or include a plurality of DUTs 44.

The measurement chamber temperature-control assembly 180 may be configured to produce a temperature-controlled thermal management fluid stream 184 and to thermally contact the temperature-controlled thermal management fluid stream with a component within, or to be supplied to, the measurement chamber internal volume (e.g., the chuck and/or the dry gas 154). For example, the measurement chamber temperature-control assembly may produce the temperature-controlled thermal management fluid stream from a thermal management fluid outlet 186 thereof and provide the temperature-controlled thermal management fluid stream to a component within the measurement chamber internal volume via a thermal management fluid conduit 182. In addition, a component within the measurement chamber internal volume may return a thermal management fluid stream 188 to the measurement chamber temperature-control assembly via a thermal management fluid inlet 190 thereof.

The measurement chamber temperature-control assembly 180 and/or the measurement chamber gas conditioner 164 may be configured to receive an exchange fluid stream 194, such as via an exchange fluid inlet 192 and/or a measurement chamber exhaust conduit 193. Gas from the measurement chamber internal volume 110, such as at least a portion of the dry gas stream 154, may be provided to the exchange fluid inlet as the exchange fluid stream (optionally via the measurement chamber exhaust conduit). Within the measurement chamber temperature-control assembly, the exchange fluid stream may exchange thermal energy with the thermal management fluid stream 188, thereby producing a heated exchange fluid stream 198 and, optionally, the temperature-controlled thermal management fluid stream 184. Within the measurement chamber gas conditioner, the exchange fluid stream may be heated (e.g., by the measurement chamber gas heater/chiller 162) to produce a heated exchange fluid stream 198. The heated exchange fluid stream may be conveyed to the access chamber gas conditioner 264 and/or the access chamber purging assembly 250 via an exchange fluid outlet 196 and/or an exchange fluid outlet conduit 197 and may be provided to the access chamber internal volume 210 as dry gas stream 254 (which is heated).

Probe systems 20 are configured to supply access chamber dry gas stream 254 (also referred to herein as dry gas stream 254) to the access chamber 200. For example, probe system 20 may include the access chamber gas conditioner 264, which is configured to provide the dry gas stream 254 to the access chamber purging assembly 250. The access chamber gas conditioner may be configured to adjust and/or control the humidity and/or the temperature of a gas, thereby transforming an access chamber source gas stream 252, which is supplied to the access chamber gas conditioner, into the access chamber dry gas stream 254, which is emitted by the access chamber gas conditioner. For example, the access chamber gas conditioner may include a dehumidifier 260 (configured to reduce and/or maintain gas humidity) and/or a gas heater/chiller 262 (configured to heat and/or chill a gas). The access chamber purging assembly may be located within and/or may be in fluid communication with the access chamber internal volume 210, and may direct the dry gas stream 254 into the access chamber internal volume and/or direct the dry gas stream 254 into fluid contact with the substrate 40 (when present in the access chamber 200). The access chamber purging assembly may be configured to create a positive pressure differential between the access chamber internal volume and the ambient environment. The access chamber purging assembly may be configured to flow the dry gas stream 254 to essentially exclude gas from the ambient environment (e.g., configured as a gas curtain).

The dry gas stream 254 may be sourced from the measurement chamber internal volume 110 and/or the dry gas stream 154, i.e., the access chamber source gas stream 252 may include a portion of the dry gas stream 154 and/or gas from the measurement chamber internal volume. For example, the probe system 20 may comprise a measurement chamber exhaust conduit 193 that is configured to convey a gas stream (e.g., a portion of the dry gas stream 154) from the measurement chamber internal volume. The conveyed gas stream may be supplied to the measurement chamber gas conditioner 164, the measurement chamber temperature-control assembly 180, the access chamber gas conditioner 264, the access chamber temperature-control assembly 280, and/or the access chamber purging assembly 250.

The access chamber source gas stream 252 may be heated to a temperature at or above a temperature of the substrate after testing in the measurement chamber (e.g., the temperature of the measurement chamber) and/or the temperature of the ambient environment surrounding the probe system 20 (e.g., above a dew point temperature and/or a frost point temperature of the ambient environment) to produce the dry gas stream 254. Although not required, it is within the scope of the present disclosure that the access chamber source gas stream may be heated by heat generated, and optionally, incidentally generated, by a portion of the probe system and/or by a component that is dedicated to heating the dry gas stream 254 and/or the access chamber source gas stream. For example, the measurement chamber gas conditioner 164, the measurement chamber temperature-control assembly 180, the access chamber gas conditioner 264, and/or the access chamber temperature-control assembly 280 may be configured to heat the dry gas stream 254 and/or the access chamber source gas stream. The component configured to heat the dry gas stream 254 also may be configured to heat and/or to cool a component of the probe system 20 and/or a component within the measurement chamber internal volume 110 (e.g., the chuck 130). For example, the measurement chamber temperature-control assembly may include a vapor-compression device with a hot side and a cold side. The cold side of the vapor-compression device may be used to cool the chuck (via suitable heat transfer mechanisms). The hot side of the vapor-compression device may be used to heat the dry gas stream 254 and/or the access chamber source gas stream (via suitable heat transfer mechanisms).

The various gas streams that are discussed herein with reference to probe systems 20 may include and/or be any suitable stream. This may include any suitable air stream, inert gas stream, and/or another gas, or fluid, stream. As an illustrative, non-exclusive example, dry gas stream 254 may include and/or be a dry air stream and also may be referred to herein as a dry air stream 254. As another illustrative, non-exclusive example, dry gas stream 154 may include and/or be a dry air stream and also may be referred to herein as a dry air stream 154. As yet another illustrative, non-exclusive example, exchange fluid stream 194 may include and/or be an air stream and also may be referred to herein as an air stream 194.

Probe systems 20 may include the access chamber temperature-control assembly 280, which is configured to adjust and/or to control the temperature of the access chamber internal volume and/or components therein (e.g., the transfer assembly 240 and/or the substrate 40). The access chamber temperature-control assembly may heat and/or cool the transfer assembly by conduction, convection, and/or radiation. For example, the access chamber temperature-control assembly 280 may supply a temperature-controlled thermal management fluid stream 284 through a thermal management fluid conduit 282 to the transfer assembly. The access chamber temperature-control assembly may include at least one of a resistive heater, a thermoelectric device, a Peltier device, a heat pump, a vapor-compression device, a refrigerant, a circulating pump, a heat-transfer fluid, and/or a heat exchanger.

Probe system 20 may include the probe assembly 170, such as a probe card and/or a plurality of probe tips, which may be configured to physically, electrically, mechanically, and/or optically contact substrate 40 and/or DUT 44 thereof. The probe assembly generally is configured to transmit a signal to and/or receive a signal from the substrate and/or the DUT. Illustrative, non-exclusive examples of probe assemblies 170 include any suitable needle probe, Pyramid-brand probe, membrane probe, space transformer, interposer, optical conduit, and/or electrical conduit.

Probe systems 20 may include a controller 300 that may be adapted, configured, and/or programmed to control the operation of at least a portion of the probe system. For example, the controller may be programmed to control the operation of the measurement chamber door 120, the chuck translation assembly 132, the measurement chamber purging assembly 150, the measurement chamber gas conditioner 164, the probe assembly 170, the measurement chamber temperature-control assembly 180, the substrate transfer assembly 240, the access chamber purging assembly 250, the access chamber gas conditioner 264, and/or the access chamber temperature control assembly 280. The controller may provide a suitable signal 330 (e.g., a control signal) to any suitable portion of probe system and/or receive another suitable signal 330 (e.g., a status signal, a data signal, and/or a resultant signal) from any suitable portion of the probe system. As an illustrative, non-exclusive example, controller 300 may be configured to control the operation of probe system 20 using any of the methods 400 that are discussed in more detail herein.

Controller 300 may include a test signal generation assembly 310 that may be configured to generate a test signal 312, which may be conveyed to DUT 44 via probe assembly 170. Upon receipt of the test signal, DUT 44 may generate a resultant signal 322, which may be conveyed to a resultant signal analysis assembly 320 of controller 300 via probe assembly 170. Additionally or alternatively, controller 300 may be programmed to control an orientation of probe assembly 170 relative to the DUT (and/or the substrate 40 including the DUT), a distance between the probe assembly and the substrate, and/or a relative orientation of a plurality of probe tips that may form a portion of the probe assembly. As an illustrative, non-exclusive example, controller 300 may do so by sending one or more control signals 330 to the probe assembly and/or to the chuck translation assembly 132.

Illustrative, non-exclusive examples of test signal generation assemblies include any suitable electrical power source, voltage generator, electric current generator, and/or function generator. Illustrative, non-exclusive examples of resultant signal analysis assemblies include any suitable impedance analyzer, network analyzer, bit error rate tester, and/or spectrum analyzer.

Controller 300 may be programmed to control a temperature, a humidity, and/or a flow rate of the dry gas stream 154 that is provided to the measurement chamber internal volume 110. This may include providing one or more control signals 330 to the measurement chamber temperature control assembly 180, the measurement chamber gas conditioner 164, the measurement chamber dehumidifier 160, and/or the measurement chamber gas heater/chiller 162 to control a temperature, a humidity, and/or a flow rate of the dry gas stream 154 therefrom. Additionally or alternatively, this may include providing one or more control signals 330 to the measurement chamber purging assembly 150 to control a flow rate of the dry gas stream 154 therethrough. It is also within the scope of the present disclosure that the flow rate of the dry gas stream 154 may be controlled based, at least in part, on the state of measurement chamber door 120. As an illustrative, non-exclusive example, controller 300 may control the flow rate of the dry gas stream 154 to one flow rate when the measurement chamber door is in the closed state and to another flow rate when the measurement chamber door is in the open state. Under these conditions, the closed state flow rate may be less than the open state flow rate, and the increase in flow rate of the dry gas stream 154 when the measurement chamber door is in the open state may restrict, and optionally prevent, a flow of contaminants, such as humidity and/or water, from access chamber 200 into measurement chamber 100.

Controller 300 may be programmed to control a temperature, a humidity, and/or a flow rate of the dry gas stream 254 that is provided to the access chamber internal volume 210. This may include providing one or more control signals 330 to the measurement chamber temperature control assembly 180, the access chamber temperature control assembly 280, the access chamber gas conditioner 264, the access chamber dehumidifier 260, and/or the access chamber gas heater/chiller 262 to control a temperature, a humidity, and/or a flow rate of the dry gas stream 254 therefrom. Additionally or alternatively, this also may include providing one or more control signals 330 to the access chamber purging assembly 250 to control a flow rate of the dry gas stream 254 therethrough. It is also within the scope of the present disclosure that the flow rate of the dry gas stream 254 may be controlled based, at least in part, on the state of measurement chamber door 120. As an illustrative, non-exclusive example, controller 300 may control the flow rate of the dry gas stream 254 to one flow rate when the measurement chamber door is in the closed state and to another flow rate when the measurement chamber door is in the open state. Under these conditions, the closed state flow rate may be greater than the open state flow rate, and the decrease in flow rate of the dry gas stream 254 when the measurement chamber door is in the open state may restrict, and optionally prevent, a flow of contaminants, such as humidity and/or water, from access chamber 200 into measurement chamber 100.

Controller 300 may be programmed to control the operation of the chuck 130 and/or the chuck translation assembly 132. For example, the controller may be configured to selectively transition the chuck between the load position 134 and the test position 136. Controller 300 may be programmed to control the operation of transfer assembly 240. This may include controlling the transfer assembly to obtain a substrate 40 from a cassette 290 that may contain a plurality of substrates 40, controlling the transfer assembly to place the substrate on the chuck (generally in the load position), controlling the transfer assembly to remove the substrate from the chuck (generally in the load position), and/or controlling the transfer assembly to return the substrate to the cassette.

Controller 300 may be programmed to control the operation of the measurement chamber temperature-control assembly 180. This may include controlling a temperature of the chuck 130. For example, the controller may be programmed to control the temperature of the temperature-controlled thermal management fluid 184 (such as to control the temperature of the chuck), controlling a flow rate of the temperature-controlled thermal management fluid, controlling a temperature of heated exchange fluid stream 198, and/or controlling a flow rate of the heated exchange fluid stream. Additionally or alternatively, controller 300 may be programmed to control the operation of the access chamber temperature-control assembly 280. This may include controlling a temperature of the transfer assembly 240 and/or of the substrate 40 when present within the access chamber internal volume 210.

Figure 2:
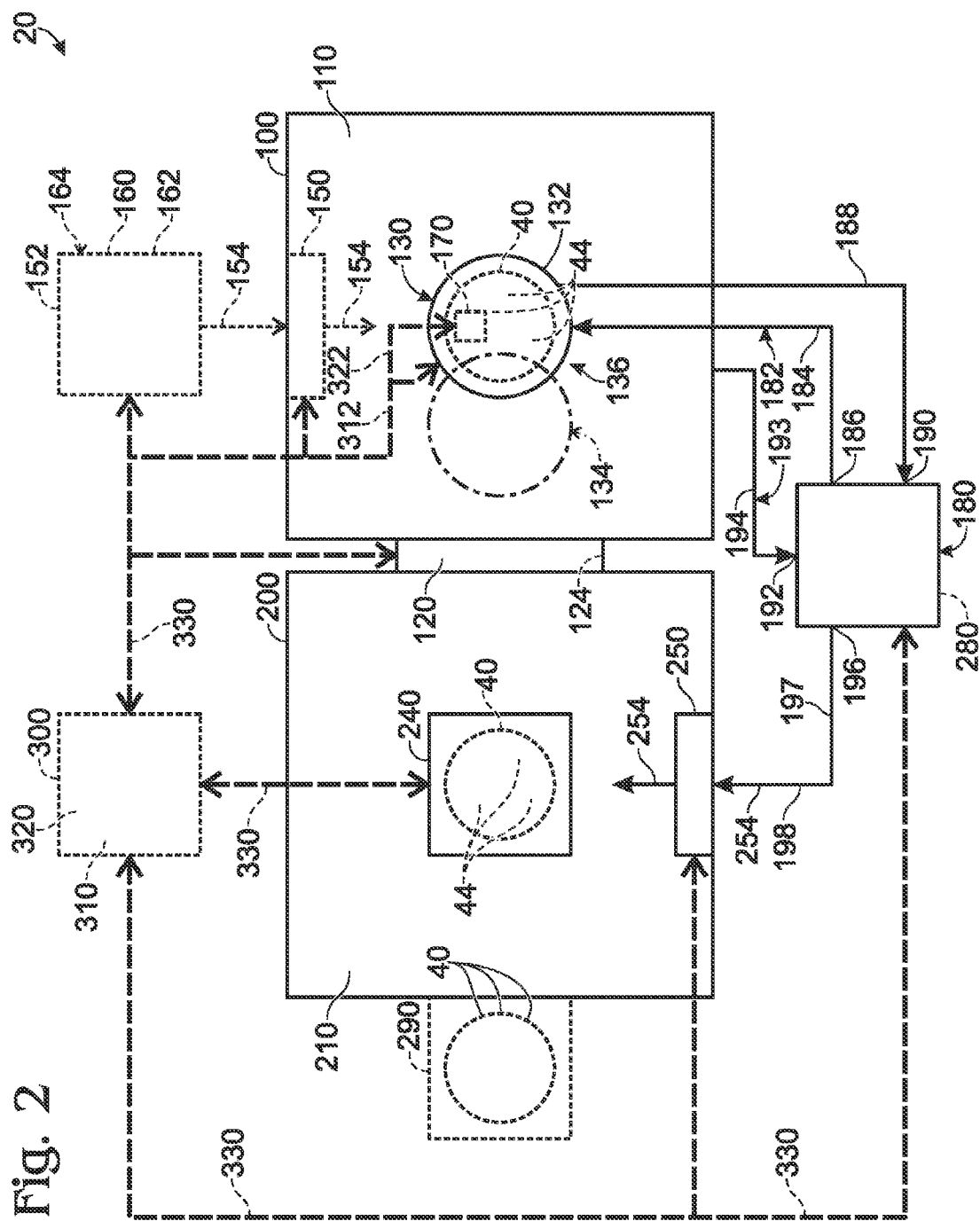
FIG. 2 is a schematic representation of illustrative, non-exclusive examples of a probe system that may be utilized with and/or include the systems and methods according to the present disclosure.

FIG. 2 is a schematic representation of illustrative, non-exclusive examples of probe systems 20 that specifically route, or flow, the measurement chamber dry gas 154 from the measurement chamber 100 and through a heat exchanger in the measurement chamber temperature control assembly 180 to generate the access chamber dry gas 254 (which is heated). In the example of FIG. 2, the measurement chamber temperature-control assembly may be configured to produce a temperature-controlled thermal management fluid stream 184 from a thermal management fluid outlet 186 thereof and to provide the temperature-controlled thermal management fluid stream to the chuck 130 via a thermal management fluid conduit 182. The chuck may receive the temperature-controlled thermal management fluid stream from the thermal management fluid conduit to control a temperature of the chuck. In addition, the chuck also may return a thermal management fluid stream 188 to the measurement chamber temperature-control assembly via a thermal management fluid inlet 190 thereof.

The measurement chamber temperature-control assembly 180 is configured to receive the exchange fluid stream 194 via the exchange fluid inlet 192 thereof. Gas from the measurement chamber internal volume 110, e.g., at least a portion of the dry gas stream 154 that was provided to the measurement chamber internal volume, is provided to the exchange fluid inlet 192 as the exchange fluid stream via the measurement chamber exhaust conduit 193. Using the heat exchanger within the measurement chamber temperature-control assembly, the exchange fluid stream exchanges thermal energy with the thermal management fluid stream 188, thereby producing a heated exchange fluid stream 198 and, optionally, the temperature-controlled thermal management fluid stream 184. As discussed herein, the measurement chamber may include a device which is configured to cool (e.g., a thermoelectric device, a Peltier device, a heat pump, and/or a vapor-compression device). Such devices generally also generate excess heat. At least a portion of the excess heat may be transferred to the exchange fluid stream with the heat exchanger. The heated exchange fluid stream may be conveyed to the access chamber purging assembly 250 via an exchange fluid outlet 196 and an exchange fluid outlet conduit 197, and may be provided to the access chamber internal volume 210 as dry gas stream 254 (which is heated).

Figure 3:
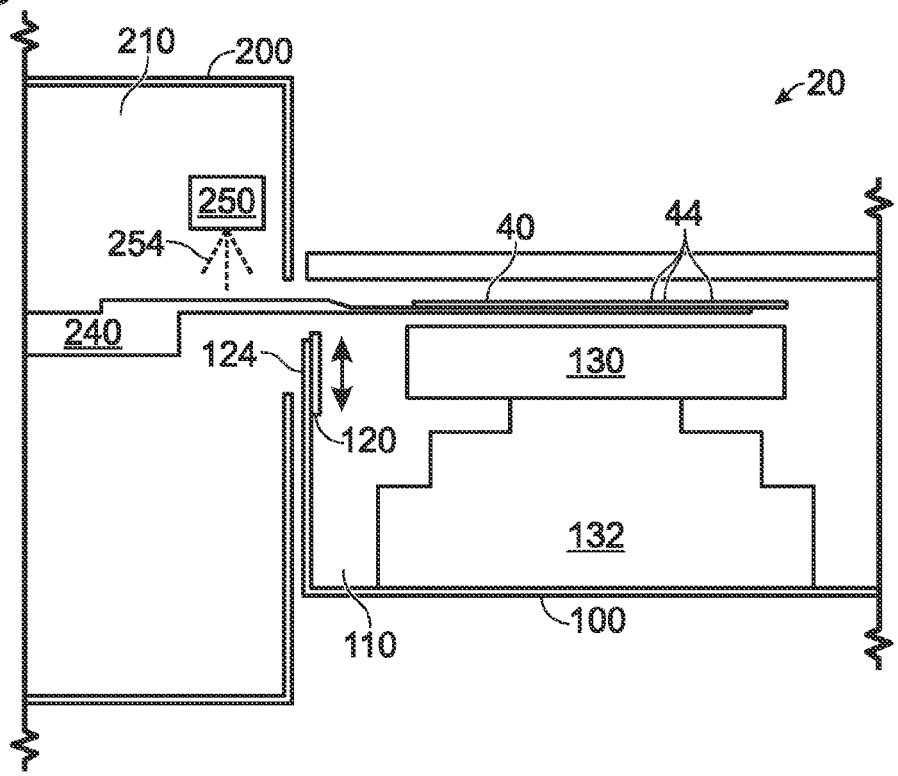
FIG. 3 is a fragmentary profile view of an illustrative, non-exclusive example of a probe system that may be utilized with and/or include the systems and methods according to the present disclosure.

FIG. 3 is a schematic representation of an illustrative, non-exclusive example of a probe system 20 which highlights transfer of the substrate 40 with the transfer assembly 240 through the measurement chamber door 120. The measurement chamber door is illustrated in an open state that allows physical transport, via the measurement chamber doorway 124, between the measurement chamber internal volume 110 and the access chamber internal volume 210. The measurement chamber door may be configured to selectively transition between the open state and a closed state that restricts physical transport between the measurement chamber internal volume 110 and the access chamber internal volume 210. The transfer assembly 240 may be generally located within the access chamber internal volume and may be configured to convey the substrate 40 through the measurement chamber door (and the measurement chamber doorway).

Figure 4:
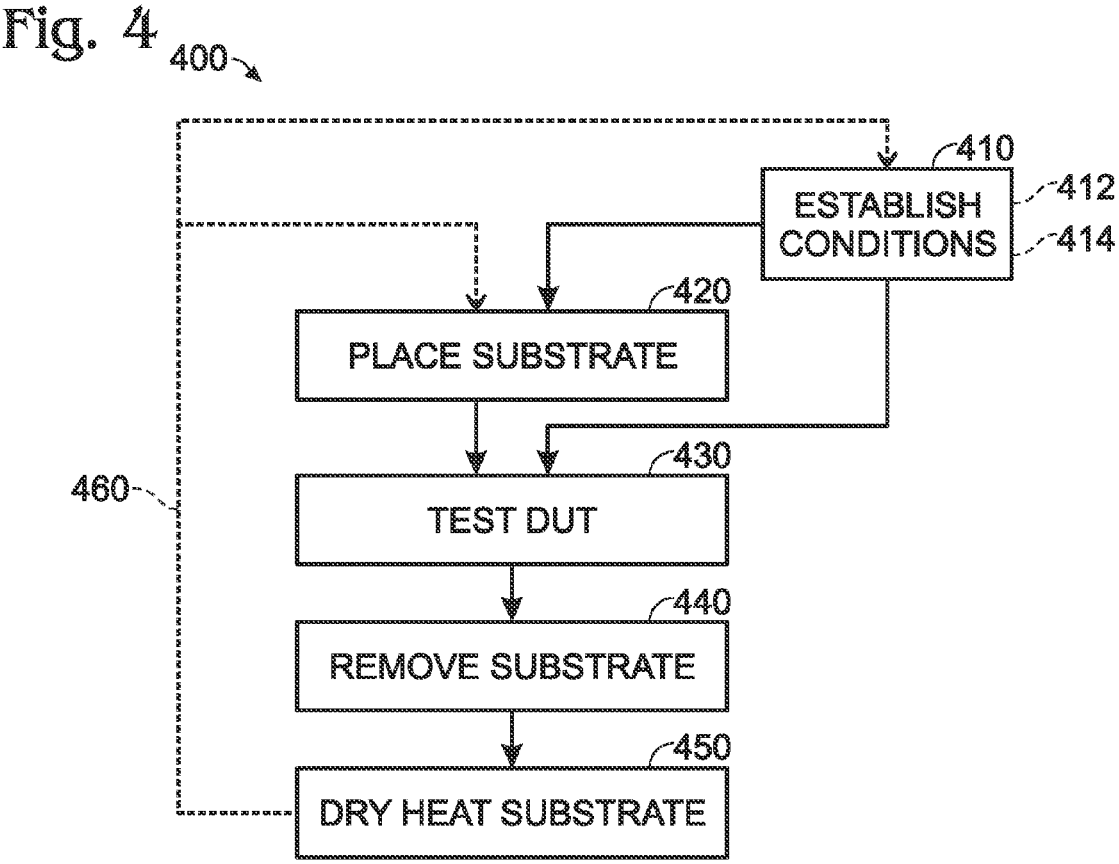
FIG. 4 is a flowchart depicting methods of testing a device under test with a probe system according to the present disclosure.

FIG. 4 is a flowchart depicting methods 400 according to the present disclosure of testing a device under test with a probe system, such as probe system 20. Methods 400 may comprise establishing 410 cool, dry measurement conditions (e.g., maintaining a measurement chamber internal volume 110 at a low temperature with a dry environment), placing 420 a substrate with a DUT into the measurement conditions (e.g., placing a substrate 40 with a DUT 44 into the measurement chamber internal volume 110), testing 430 the DUT under the measurement conditions, removing 440 the substrate from the measurement conditions (e.g., removing the substrate 40 from the measurement chamber internal volume 110), and dry heating 450 the substrate (e.g., by directing a dry gas stream 254, which is heated, into fluid contact with the substrate 40).

Establishing 410 generally includes creating, controlling, and/or maintaining a low temperature environment separate from the ambient environment. Establishing 410 may include purging 412 an internal volume of a measurement chamber with a dry gas and/or setting 414 a temperature within the internal volume of the measurement chamber (e.g., setting the temperature of a temperature-controlled chuck that is located within the internal volume of the measurement chamber and/or purging the internal volume of the measurement chamber with a gas at a predetermined, preselected, or otherwise established temperature). Establishing 410 may be performed before, during, and/or after the placing 420. Generally, establishing 410 is complete before testing 430 begins, though maintenance of the measurement conditions may begin and/or continue during testing 430 and other steps of methods 400.

Establishing 410 may be initiated, adjusted, and/or controlled based as least in part on the state of the probe system (e.g., the location of the substrate 40 with respect to the probe system 20, the state of a measurement chamber door 120, the position of a chuck 130, and/or the position of a transfer assembly 240). For example, where establishing 410 includes purging 412, purging 412 may be performed at a first gas flow rate when the measurement chamber door is in a closed state and may be performed at a second gas flow rate, which is greater than the first gas flow rate, when the measurement chamber door is in an open state.

Where establishing 410 includes purging 412, purging 412 may include providing a dry gas stream (e.g., dry gas stream 154) to the internal volume of the measurement chamber. Further, purging 412 may include providing a temperature-controlled gas stream to the internal volume of the measurement chamber. Purging 412 may include intermittently or continuously purging the internal volume of the measurement chamber. Additionally or alternatively, purging 412 may include varying a flow rate of the dry gas steam, optionally based upon the state of the probe system.

Establishing 410 may include setting 414 a temperature within the internal volume of the measurement chamber to a low temperature, i.e., setting a temperature of the measurement chamber internal volume and/or setting a temperature of a component within the measurement chamber internal volume that is configured to thermally contact the substrate. The low temperature created, controlled, and/or maintained through the establishing 410 is less than a dew point temperature and/or a frost point temperature of the ambient environment that surrounds the probe system. As illustrative, non-exclusive examples, the low temperature may be less than 50° C., less than 40° C., less than 30° C., less than 20° C., less than 10° C., less than 0° C., less than –10° C., less than –20° C., less than –30° C., less than –40° C., less than –50° C., less than –60° C., less than –70° C., less than –80° C., greater than –120° C., greater than –110° C., greater than –100° C., greater than –90° C., greater than –80° C., greater than –70° C., greater than –60° C., greater than –50° C., –120° C.-50° C., –80° C.-0° C., and/or –80° C.--30° C.

Establishing 410 may include setting 414 a temperature within the internal volume of the measurement chamber to an elevated temperature that is greater than the temperature of the ambient environment that surrounds the probe system. As illustrative, non-exclusive examples, the elevated temperature may be greater than 0° C., greater than 25° C., greater than 50° C., greater than 75° C., greater than 100° C., greater than 125° C., greater than 150° C., greater than 175° C., greater than 200° C., greater than 225° C., greater than 250° C., less than 400° C., less than 375° C., less than 350° C., less than 325° C., less than 300° C., less than 275° C., less than 250° C., less than 225° C., less than 200° C., 0° C.-400° C., 25° C.-250° C., and/or 50° C.-200° C.

Methods 400 include placing 420 the substrate (which may be or include one or more DUTs) into the measurement conditions (i.e., into a volume that includes, or will include, the measurement conditions resulting from establishing 410) prior to testing 430. For example, the substrate may be placed on the chuck within a measurement chamber internal volume. Generally, placing 420 includes moving the substrate from one volume (e.g., an access chamber internal volume) to another volume (e.g., the measurement chamber internal volume) that is, or will be, environmentally controlled. For example, placing 420 may include moving the substrate with the transfer assembly 240 and/or moving the chuck 130 to a load position 134 prior to placing the substrate on the chuck.

Placing 420 may include traversing a doorway between an access chamber and the measurement chamber (e.g., the measurement chamber doorway 124 of the measurement chamber door 120). For example, placing 420 may include moving the substrate from the access chamber internal volume 210, through the measurement chamber door 120, and into the measurement chamber internal volume 110. Where the door has an open state (i.e., a state allowing physical transport through the door), placing 420 may include establishing, maintaining, and/or creating the open state. Where the door also has a closed state (i.e., a state configured to isolate, fluidically and/or thermally, the internal volume of the access chamber from the internal volume of the measurement chamber), placing 420 may include transitioning the door from the closed state to the open state, and/or from the open state to the closed state. For example, placing 420 may include transitioning the measurement chamber door 120 between the open state and the closed state. Operation of the door generally may be performed based upon any suitable criteria and/or at any suitable point in time during methods 400. As an illustrative, non-exclusive example, placing 420 may include transitioning the door to an open state, and/or ensuring the door is in an open state prior to moving the substrate from the access chamber to the measurement chamber. As another illustrative, non-exclusive example, placing 420 may include transitioning the door to a closed state, and/or ensuring the door is in a closed state, after moving the substrate form the access chamber to the measurement chamber.

Methods 400 include testing 430 the DUT, which is or is included on the substrate, under measurement conditions established by the establishing 410. Testing 430 may include testing the DUT in any suitable manner (e.g., electrically, optically, and/or mechanically). As illustrative, non-exclusive examples, testing 430 may include moving the chuck 130 to a test position 136 subsequent to placing 420, and/or contacting the DUT with a probe tip of a probe assembly 170 subsequent to placing 420. Where the substrate includes a plurality of DUTs, testing 430 may include testing at least two of the DUTs, the majority of the DUTs, and/or all of the DUTs. Where testing 430 includes testing more than one DUT, each DUT independently may be tested at least partially concurrently and/or at least partially sequentially with another DUT.

Methods 400 include removing 440 the substrate from the measurement conditions (i.e., a volume that includes the measurement conditions resulting from establishing 410) subsequent to testing 430. For example, the substrate may be removed from the chuck within the measurement chamber internal volume. Generally, removing 440 includes moving the substrate from one volume (e.g., the measurement chamber internal volume), which is environmentally controlled, to another volume (e.g., the access chamber internal volume) that is, or will be, at least partially subject to ambient environmental conditions. For example, removing 440 may include moving the substrate with the transfer assembly 240 and/or moving the chuck 130 to the load position 134 prior to removing the substrate from the chuck.

Removing 440 may include traversing a doorway between the access chamber and the measurement chamber (e.g., the measurement chamber doorway 124 of the measurement chamber door 120). For example, removing 440 may include moving the substrate from the measurement chamber internal volume 110, through the measurement chamber door 120, and into the access chamber internal volume 210. Where the door has an open state (i.e., a state allowing physical transport through the door), removing 440 may include establishing, maintaining, and/or creating the open state. Where the door also has a closed state (i.e., a state configured to isolate, fluidically and/or thermally, the internal volume of the access chamber from the internal volume of the measurement chamber), removing 440 may include transitioning the door from the closed state to the open state, and/or from the open state to the closed state. For example, removing 440 may include transitioning the measurement chamber door 120 between the open state and the closed state. Operation of the door generally may be performed based upon any suitable criteria and/or at any suitable point in time during methods 400. As an illustrative, non-exclusive example, removing 440 may include transitioning the door to an open state and/or ensuring the door is in an open state prior to moving the substrate from the measurement chamber to the access chamber. As another illustrative, non-exclusive example, removing 440 may include transitioning the door to a closed state and/or ensuring the door is in a closed state, after moving the substrate from the measurement chamber to the access chamber.

Methods 400 include dry heating 450 the substrate (i.e., heating the substrate in a dry environment) subsequent to testing 430. Dry heating 450 generally includes creating, controlling, and/or maintaining a dry environment in fluid contact with the substrate while the substrate transitions from a low temperature (due to the measurement conditions) to a temperature above a dew point temperature and/or a frost point temperature of the ambient environment. Dry heating 450 may include directing a dry gas stream (e.g., dry gas stream 254) into fluid contact with the substrate. For example, dry heating 450 may include providing a dry gas stream to the internal volume of the access chamber that contains the substrate. Dry heating 450 includes heating the substrate. The heating may be active and/or passive heating, for example, heating by conduction, convection, and/or radiation. Where the substrate is within the internal volume of the access chamber, dry heating 450 may include setting the temperature of the internal volume, or a component therein, above the dew point temperature and/or the frost point temperature of the ambient environment (e.g., at or above the temperature of the ambient environment). Additionally or alternatively, dry heating 450 may include thermally contacting the substrate with material that is above the dew point temperature and/or the frost point temperature of the ambient environment and/or a local environment surrounding the substrate. For example, dry heating 450 may include contacting the substrate with a dry gas and/or the transfer assembly (e.g., transfer assembly 240) that is (are) at least initially warmer than the substrate.

Dry heating 450 generally is performed when the substrate is in a different location than the location for testing 430 (e.g., at the test position 136). For example, dry heating 450 may be performed while the substrate is at least partially within the access chamber internal volume (and hence at least partially outside the measurement chamber internal volume). Dry heating 450 may continue until the substrate is at a desired temperature and/or may continue for a predetermined time. Dry heating 450 may be performed as the substrate is moving, for example during removing 440. Dry heating 450 may be initiated with, and/or as a result of, removing 440. Preparation for dry heating 450 (e.g., establishing, controlling, and/or maintaining a dry and/or warm environment) may be performed at any suitable time during methods 400. For example, the access chamber internal volume 210 may be purged with warm, dry gas during testing 430 (prior to removing 440) and/or during removing 440.

Methods 400 may include repeating 460 at least placing 420, testing 430, and removing 440. Repeating 460 generally includes dry heating 450. Repeating 460 may include repeating with the same substrate and/or with a series of different substrates. For example, methods 400 may include placing 420 a first substrate with a DUT, testing 430 the DUT on the first substrate, removing 440 the first substrate, dry heating 450 the first substrate, placing 420 a second substrate with a DUT, testing 430 the DUT on the second substrate, removing 440 the second substrate, and dry heating 450 the second substrate.

Repeating 460 may include establishing 410 measurement conditions that are independently the same or different for each repeat, provided that at least one measurement condition includes a low temperature (lower than the dew point temperature and/or the frost point temperature of the ambient environment) in a dry environment (where the dew point temperature and/or the frost point temperature is lower than the local temperature). For example, a plurality of substrates may be sequentially placed into, tested in, and removed from a first measurement environment with cool, dry measurement conditions, and (previously or subsequently) may be sequentially (in the same or different order) placed into, tested in, and removed from a second measurement environment different from the first measurement environment. The second measurement environment may include an elevated temperature (a temperature greater than the dew point temperature and/or the frost point temperature of the ambient environment). No dry heating 450 may be needed for a substrate that was tested at an elevated temperature.

Repeating 460 may include performing at least one of placing 420, testing 430, removing 440, and dry heating 450 for one substrate at least partially concurrently with at least one of removing 440 and dry heating 450 for another substrate. For example, one substrate may be placed while another substrate is removed. As another example, one substrate may be dry heated while another substrate is tested.

In the present disclosure, several of the illustrative, non-exclusive examples have been discussed and/or presented in the context of flow diagrams, or flow charts, in which the methods are shown and described as a series of blocks, or steps. Unless specifically set forth in the accompanying description, it is within the scope of the present disclosure that the order of the blocks may vary from the illustrated order in the flow diagram, including with two or more of the blocks (or steps) occurring in a different order and/or concurrently. It is also within the scope of the present disclosure that the blocks, or steps, may be implemented as logic, which also may be described as implementing the blocks, or steps, as logics. In some applications, the blocks, or steps, may represent expressions and/or actions to be performed by functionally equivalent circuits or other logic devices. The illustrated blocks may, but are not required to, represent executable instructions that cause a computer, processor, and/or other logic device to respond, to perform an action, to change states, to generate an output or display, and/or to make decisions.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and define a term in a manner or are otherwise inconsistent with either the non-incorporated portion of the present disclosure or with any of the other incorporated references, the non-incorporated portion of the present disclosure shall control, and the term or incorporated disclosure therein shall only control with respect to the reference in which the term is defined and/or the incorporated disclosure was originally present.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

Illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1. A probe system, comprising:

a measurement chamber that defines a measurement chamber internal volume;

a measurement chamber temperature-control assembly that is configured to cool a substrate within the measurement chamber internal volume to a temperature below a dew point temperature and/or a frost point temperature of an ambient environment surrounding the probe system;

an access chamber that defines an access chamber internal volume;

a measurement chamber door that is configured to selectively isolate the measurement chamber internal volume from the access chamber internal volume;

a transfer assembly that is configured to selectively transfer the substrate through the measurement chamber door and thus between the measurement chamber internal volume and the access chamber internal volume; and an access chamber purging assembly that is configured to selectively direct an access chamber dry gas stream in fluid contact with the substrate when the substrate is located within the access chamber internal volume.

A2. The probe system of paragraph A1, further comprising a chuck that is located within the measurement chamber internal volume.

A2.1. The probe system of paragraph A2, wherein the chuck is a temperature-controlled chuck.

A2.2. The probe system of any of paragraphs A2-A2.1, wherein the measurement chamber temperature-control assembly is configured to cool the chuck to a temperature below the dew point temperature and/or the frost point temperature.

A2.3. The probe system of any of paragraphs A2-A2.2, wherein the measurement chamber temperature-control assembly is configured to heat the chuck to a temperature approximately equal to or greater than a temperature of the ambient environment.

A2.4. The probe system of any of paragraphs A2-A2.3, wherein the measurement chamber temperature-control assembly is configured to produce a temperature-controlled thermal management fluid stream, wherein the probe system further includes a thermal management fluid conduit that is configured to direct the temperature-controlled thermal management fluid stream in thermal contact with the chuck to control a temperature of the chuck.

A3. The probe system of any of paragraphs A1-A2.4, wherein the measurement chamber door is configured to fluidically isolate the measurement chamber internal volume from the access chamber internal volume.

A4. The probe system of any of paragraphs A1-A3, wherein the measurement chamber door is configured to thermally isolate the measurement chamber internal volume from the access chamber internal volume.

A5. The probe system of any of paragraphs A1-A4, wherein the measurement chamber door at least partially spans a measurement chamber doorway between the measurement chamber and the access chamber.

A5.1. The probe system of paragraph A5, wherein the transfer assembly is configured to selectively transfer the substrate through the measurement chamber doorway.

A6. The probe system of any of paragraphs A1-A5.1, wherein the measurement chamber door includes, and optionally is, a gas curtain.

A7. The probe system of any of paragraphs A1-A6, wherein the measurement chamber door has an open state configured to allow physical transport between the measurement chamber internal volume and the access chamber internal volume.

A8. The probe system of any of paragraphs A1-A7, wherein the measurement chamber door has a closed state configured to isolate the measurement chamber internal volume and the access chamber internal volume.

A9. The probe system of any of paragraphs A1-A8, further comprising a measurement chamber purging assembly that is configured to direct a measurement chamber dry gas stream into the measurement chamber internal volume.

A9.1. The probe system of paragraph A9, wherein the measurement chamber purging assembly is configured to flow the measurement chamber dry gas stream to essentially exclude from the measurement chamber internal volume gas from the ambient environment.

A9.2. The probe system of any of paragraphs A9-A9.1, wherein the measurement chamber purging assembly is configured to create a positive pressure differential between the measurement chamber internal volume and the ambient environment.

A10. The probe system of any of paragraphs A1-A9.2, wherein the probe system further includes a measurement chamber gas conditioner that is configured to provide a/the measurement chamber dry gas stream to the measurement chamber internal volume.

A10.1. The probe system of paragraph A10, wherein the measurement chamber gas conditioner is configured to adjust and/or control a humidity and/or a temperature of the measurement chamber dry gas stream.

A10.2. The probe system of any of paragraphs A10-A10.1, wherein the measurement chamber gas conditioner includes a dehumidifier.

A10.3. The probe system of any of paragraphs A10-A10.2, wherein the measurement chamber gas conditioner includes a gas heater/chiller.

A10.4. The probe system of any of paragraphs A10-A10.3, wherein the measurement chamber gas conditioner includes a gas chiller.

A11. The probe system of any of paragraphs A1-A10.4, wherein the access chamber dry gas stream is a heated access chamber dry gas stream.

A12. The probe system of any of paragraphs A1-A11, wherein the probe system further includes an access chamber gas conditioner that is configured to provide the access chamber dry gas stream to the access chamber purging assembly.

A12.1. The probe system of paragraph A12, wherein the access chamber gas conditioner is configured to adjust and/or control a humidity and/or a temperature of the access chamber dry gas stream.

A12.2. The probe system of any of paragraphs A12-A12.1, wherein the access chamber gas conditioner includes a dehumidifier.

A12.3. The probe system of any of paragraphs A12-A12.2, wherein the access chamber gas conditioner includes a gas heater/chiller.

A12.4. The probe system of any of paragraphs A12-A12.3, wherein the access chamber gas conditioner includes a gas heater.

A12.5. The probe system of any of paragraphs A12-A12.4, wherein the access chamber gas conditioner is configured to produce a/the heated access chamber dry gas stream.

A12.6. The probe system of any of paragraphs A12-A12.5, wherein the access chamber gas conditioner is configured to accept an access chamber source gas stream and to transform the access chamber source gas stream into the access chamber dry gas stream by at least one of drying and heating.

A13. The probe system of any of paragraphs A1-A12.6, wherein the measurement chamber temperature-control assembly is configured to heat an/the access chamber source gas stream to produce a/the heated access chamber dry gas stream.

A13.1. The probe system of paragraph A13, wherein the access chamber source gas stream includes a portion of a/the measurement chamber dry gas stream.

A14. The probe system of any of paragraphs A1-A13.1, wherein the probe system further comprises a measurement chamber exhaust conduit that is configured to convey a gas stream from the measurement chamber internal volume to an/the access chamber gas conditioner as an access chamber source gas stream.

A15. The probe system of any of paragraphs A1-A14, wherein the measurement chamber temperature-control assembly is configured to heat the substrate within the measurement chamber internal volume.

A16. The probe system of any of paragraphs A1-A15, wherein the measurement chamber temperature-control assembly includes:

a thermal management fluid inlet that is configured to receive a thermal management fluid stream;

a thermal management fluid outlet that is configured to produce a/the temperature-controlled thermal management fluid stream;

an exchange fluid inlet that is configured to receive an exchange fluid stream; and an exchange fluid outlet that is configured to produce a heated exchange fluid stream;

wherein the measurement chamber temperature-control assembly is configured to exchange thermal energy between the thermal management fluid stream and the exchange fluid stream to produce the temperature-controlled thermal management fluid stream and the heated exchange fluid stream, and wherein the measurement chamber temperature-control assembly is configured to cool the substrate within the measurement chamber internal volume with the temperature-controlled thermal management fluid stream.

A16.1. The probe system of paragraph A16, wherein the probe system further comprises a/the measurement chamber exhaust conduit that is configured to convey a gas stream from the measurement chamber internal volume and provide the gas stream to the exchange fluid inlet of the measurement chamber temperature-control assembly as the exchange fluid stream.

A16.2. The probe system of any of paragraphs A16-A16.1, wherein the probe system further comprises an exchange fluid outlet conduit that is configured to receive the heated exchange fluid stream from the exchange fluid outlet and convey the heated exchange fluid stream to the access chamber purging assembly as the access chamber dry gas stream.

A16.3. The probe system of any of paragraphs A16-A16.2, wherein the measurement chamber temperature-control assembly is configured to heat the substrate within the measurement chamber internal volume with the temperature-controlled thermal management fluid stream.

A17. The probe system of any of paragraphs A1-A16.3, wherein the probe system further includes a controller that is configured to control the operation of the probe system, optionally using the method of any of paragraphs B1-B31.4.

A17.1. The probe system of paragraph A17, wherein the probe system further includes a test signal generation assembly that is configured to generate a test signal.

A17.2. The probe system of any of paragraphs A17-A17.1, wherein the probe system further includes a resultant signal analysis assembly that is configured to receive a resultant signal from a device under test that is present on the substrate.

A18. The probe system of any of paragraphs A1-A17.2, wherein the probe system further includes a probe assembly that is configured to at least one of convey a/the test signal to a/the device under test and receive a/the resultant signal from the device under test.

A19. The probe system of any of paragraphs A1-A18, wherein the access chamber dry gas stream includes a dry air stream, optionally wherein a/the measurement chamber dry gas stream includes a dry air stream, optionally wherein a/the exchange fluid stream includes an air stream, and optionally wherein a/the heated exchange fluid stream includes a heated air stream.

A20. The probe system of any of paragraphs A1-A19, wherein the substrate includes, optionally is, at least one of a wafer, a chip, a semiconductor wafer, a semiconductor chip, a silicon wafer, a silicon chip, a Group III-V semiconductor wafer, a Group III-V semiconductor chip, and a printed circuit.

B1. A method of testing a device under test (DUT) with a probe system including a measurement chamber, the method comprising:
establishing a low temperature and a dry environment within a measurement chamber internal volume of the measurement chamber;
placing a substrate with a DUT into the measurement chamber internal volume;
testing the DUT;
removing the substrate from the measurement chamber internal volume; and
dry heating the substrate at least partially outside of the measurement chamber internal volume.

B2. The method of paragraph B1, wherein the low temperature is less than a dew point temperature and/or a frost point temperature of an ambient environment that surrounds the probe system.

B3. The method of any of paragraphs B1-B2, wherein the low temperature is a temperature of the measurement chamber internal volume and/or a temperature of a component within the measurement chamber internal volume that is configured to thermally contact the substrate.

B4. The method of any of paragraphs B1-B3, wherein the establishing creates a dry environment in the measurement chamber internal volume, wherein the dry environment has a dew point temperature and/or a frost point temperature that is below the low temperature.

B5. The method of any of paragraphs B1-B4, wherein the low temperature is less than 50° C., less than 40° C., less than 30° C., less than 20° C., less than 10° C., less than 0° C., less than −10° C., less than −20° C., less than −30° C., less than −40° C., less than −50° C., less than −60° C., less than −70° C., less than −80° C., greater than −120° C., greater than −110° C., greater than −100° C., greater than −90° C., greater than −80° C., greater than −70° C., greater than −60° C., greater than −50° C., −120° C.-50° C., −80° C.-0° C., and/or −80° C.−−30° C.

B6. The method of any of paragraphs B1-B5, wherein the establishing includes controlling and/or maintaining a temperature of a chuck, which is located within the measurement chamber internal volume, at the low temperature.

B7. The method of any of paragraphs B1-B6, wherein the establishing includes maintaining the low temperature and the dry environment within the measurement chamber internal volume, and optionally maintaining during at least one of placing, testing, removing, and dry heating.

B8. The method of any of paragraphs B1-B7, wherein the establishing includes purging, and optionally continuously purging, the measurement chamber internal volume with a measurement chamber dry gas stream.

B9. The method of any of paragraphs B1-B8, wherein the probe system includes a measurement chamber door, and wherein the establishing includes closing the measurement chamber door and/or maintaining the measurement chamber door in a closed state.

B9.1. The method of paragraph B9, wherein the establishing includes purging the measurement chamber internal volume at a first gas flow rate when the measurement chamber door is closed and purging the measurement chamber internal volume at a second gas flow rate when the measurement chamber door is open, wherein the first gas flow rate is less than the second gas flow rate.

B10. The method of any of paragraphs B1-B9.1, wherein the placing includes moving the substrate from an access chamber internal volume of an access chamber of the probe system, through a/the measurement chamber door of the probe system, and into the measurement chamber internal volume.

B10.1. The method of paragraph B10, wherein the placing includes opening the measurement chamber door prior to moving the substrate through the measurement chamber door.

B10.2. The method of any of paragraphs B10-B10.1, wherein the placing includes closing the measurement chamber door after moving the substrate through the measurement chamber door.

B11. The method of any of paragraphs B1-B10.2, wherein the placing includes moving the substrate with a transfer assembly.

B12. The method of any of paragraphs B1-B11, wherein the placing includes placing the substrate on a/the chuck located within the measurement chamber internal volume.

B12.1. The method of paragraph B12, wherein the placing includes moving the chuck to a load position prior to placing the substrate on the chuck.

B12.2. The method of any of paragraphs B12-B12.1, wherein the placing includes moving the chuck to a test position after placing the substrate on the chuck.

B13. The method of any of paragraphs B1-B12.2, wherein the testing includes testing subsequent to the establishing and the placing.

B14. The method of any of paragraphs B1-B13, wherein the testing includes testing prior to the removing.

B15. The method of any of paragraphs B1-B14, wherein the testing includes contacting the substrate with a probe assembly of the probe system.

B16. The method of any of paragraphs B1-B15, wherein the testing includes at least one of electrically testing the DUT, optically testing the DUT, and mechanically testing the DUT.

B17. The method of any of paragraphs B1-B16, wherein the removing includes removing the substrate from a/the chuck located within the measurement chamber internal volume.

B18. The method of any of paragraphs B1-B17, wherein the removing includes moving the substrate from the measurement chamber internal volume, through a/the measurement chamber door of the probe system, and into an/the access chamber internal volume of an/the access chamber of the probe system.

B18.1. The method of paragraph B18, wherein the removing includes opening the measurement chamber door prior to moving the substrate through the measurement chamber door.

B18.2. The method of any of paragraphs B18-B18.1, wherein the removing includes closing the measurement chamber door after moving the substrate through the measurement chamber door.

B19. The method of any of paragraphs B1-B18.2, wherein the removing includes removing the substrate from a/the chuck located within the measurement chamber internal volume.

B19.1. The method of paragraph B19, wherein the removing includes moving the chuck to a load position prior to removing the substrate from the chuck.

B20. The method of any of paragraphs B1-B19.1, wherein the removing includes moving the substrate with a/the transfer assembly.

B21. The method of any of paragraphs B1-B20, wherein the method includes performing the dry heating while at least partially isolating the substrate from an/the ambient environment that surrounds the probe system.

B22. The method of any of paragraphs B1-B21, wherein the dry heating includes fluidically contacting the substrate with a dry gas.

B23. The method of any of paragraphs B1-B22, wherein the dry heating includes selectively directing an access chamber dry gas stream that is warmer than the substrate into fluid contact with the substrate to heat the substrate.

B24. The method of any of paragraphs B1-B23, wherein the dry heating includes heating the substrate for at least a predetermined time.

B25. The method of any of paragraphs B1-B24, wherein the dry heating includes heating the substrate to a temperature above a dew point temperature and/or a frost point temperature of a local environment that surrounds the substrate.

B26. The method of any of paragraphs B1-B25, wherein the dry heating includes heating the substrate to a temperature above a dew point temperature and/or a frost point temperature of an/the ambient environment that surrounds the probe system.

B27. The method of any of paragraphs B1-B26, wherein the dry heating includes heating the substrate to a temperature at or above a temperature of an/the ambient environment that surrounds the probe system.

B28. The method of any of paragraphs B1-B27, wherein the dry heating includes heating at least partially concurrently with the removing.

B29. The method of any of paragraphs B1-B28, wherein the dry heating includes heating subsequent to the testing.

B30. The method of any of paragraphs B1-B29, wherein the substrate is a first substrate of a plurality of substrates, and wherein the method further comprises repeating the placing, the testing, the removing, and the dry heating for each substrate of the plurality of substrates.

B30.1. The method of paragraph B30, wherein the plurality of substrates includes a second substrate, and wherein the placing, with respect to the second substrate, is at least partially concurrent with the removing, with respect to the first substrate.

B30.2. The method of any of paragraphs B30-B30.1, wherein the plurality of substrates includes a/the second substrate, and wherein the placing, with respect to the second substrate, is at least partially concurrent with the dry heating, with respect to the first substrate.

B30.3. The method of any of paragraphs B30-B30.2, wherein the plurality of substrates includes a/the second substrate, and wherein the testing, with respect to the second substrate, is at least partially concurrent with the dry heating, with respect to the first substrate.

B31. The method of any of paragraphs B1-B30.3, wherein the method further comprises establishing, subsequent to the testing, a second temperature within the measurement chamber that is different than the low temperature, and subsequently repeating the placing, the testing, and the removing.

B31.1. The method of paragraph B31, wherein the second temperature is an elevated temperature, optionally that is greater than 0° C., greater than 25° C., greater than 50° C., greater than 75° C., greater than 100° C., greater than 125° C., greater than 150° C., greater than 175° C., greater than 200° C., greater than 225° C., greater than 250° C., less than 400° C., less than 375° C., less than 350° C., less than 325° C., less than 300° C., less than 275° C., less than 250° C., less than 225° C., less than 200° C., 0° C.-400° C., 25° C.-250° C., and/or 50° C.-200° C.

B31.2. The method of any of paragraphs B31-B31.1, wherein the substrate is a/the first substrate of a/the plurality of substrates, and wherein the method further comprises repeating, at the second temperature, the placing, the testing, and the removing for each substrate of the plurality of substrates.

B31.3. The method of any of paragraphs B31-B31.2, wherein the substrate is a/the first substrate of a/the plurality of substrates, and wherein the method comprises repeating, at the low temperature, the placing, the testing, the removing, and the dry heating for each substrate of the plurality of substrates, and further comprises repeating, at the second temperature, the placing, the testing, and the removing for each substrate of the plurality of substrates.

B31.4. The method of any of paragraphs B31-B31.3, wherein the substrate is a/the first substrate of a/the plurality of substrates, and wherein the method comprises repeating, at the low temperature, the placing, the testing, the removing, and the dry heating for each substrate of the plurality of substrates, and, after all substrates of the plurality of substrates have been tested at the low temperature, further comprises repeating, at the second temperature, the placing, the testing, and the removing for each substrate of the plurality of substrates.

INDUSTRIAL APPLICABILITY

The systems and methods disclosed herein are applicable to the semiconductor and electronic device development, manufacturing, and test industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure, the preceding numbered paragraphs, or subsequently filed claims recite "a" or "a first" element or the equivalent thereof, such claims should be understood to include incorporation of one or more such elements, neither requiring nor excluding two or more such elements.

Applicant reserves the right to submit claims directed to certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure.

The invention claimed is:

1. A probe system for testing a device under test (DUT) that is present on a substrate, the probe system comprising:
   a measurement chamber that defines a measurement chamber internal volume;
   a chuck that is located within the measurement chamber internal volume and configured to support the substrate;
   a measurement chamber temperature-control assembly that is configured to cool the chuck and the substrate within the measurement chamber internal volume to a temperature below a dew point temperature of an ambient environment surrounding the probe system;
   a test signal generation assembly that is configured to generate a test signal;
   a resultant signal analysis assembly that is configured to receive a resultant signal from the DUT;
   a probe assembly that extends within the measurement chamber internal volume and is configured to at least one of convey the test signal to the DUT and receive the resultant signal from the DUT;
   a measurement chamber purging assembly that is configured to direct a measurement chamber dry gas stream into the measurement chamber internal volume and to create a positive pressure differential between the measurement chamber internal volume and the ambient environment during testing of the DUT;
   an access chamber that defines an access chamber internal volume;
   a measurement chamber door that is configured to selectively isolate the measurement chamber internal volume from the access chamber internal volume;
   a transfer assembly that is configured to selectively transfer the substrate through the measurement chamber door and thus between the measurement chamber internal volume and the access chamber internal volume; and
   an access chamber purging assembly that is configured to selectively direct a heated access chamber dry gas stream in fluid contact with the substrate when the substrate is located within the access chamber internal volume.

2. The probe system of claim 1, wherein the measurement chamber temperature-control assembly includes:
   a thermal management fluid inlet that is configured to receive a thermal management fluid stream;
   a thermal management fluid outlet that is configured to produce a temperature-controlled thermal management fluid stream;
   an exchange fluid inlet that is configured to receive an exchange fluid stream; and
   an exchange fluid outlet that is configured to produce a heated exchange fluid stream;
   wherein the measurement chamber temperature-control assembly is configured to exchange thermal energy between the thermal management fluid stream and the exchange fluid stream to produce the temperature-controlled thermal management fluid stream and the heated exchange fluid stream, and wherein the measurement chamber temperature-control assembly is configured to cool the substrate within the measurement chamber internal volume with the temperature-controlled thermal management fluid stream.

3. The probe system of claim 2, wherein the probe system further comprises a measurement chamber exhaust conduit that is configured to convey a gas stream from the measurement chamber internal volume and provide the gas stream to the exchange fluid inlet of the measurement chamber temperature-control assembly as the exchange fluid stream.

4. The probe system of claim 2, wherein the probe system further comprises an exchange fluid outlet conduit that is configured to receive the heated exchange fluid stream from the exchange fluid outlet and convey the heated exchange fluid stream to the access chamber purging assembly as the heated access chamber dry gas stream.

5. A probe system for testing a device under test (DUT) that is present on a substrate, the probe system comprising:
   a measurement chamber that defines a measurement chamber internal volume;
   a measurement chamber temperature-control assembly that is configured to cool the substrate within the measurement chamber internal volume to a temperature below a dew point temperature of an ambient environment surrounding the probe system;
   a test signal generation assembly that is configured to generate a test signal;
   a resultant signal analysis assembly that is configured to receive a resultant signal from the DUT;
   a probe assembly that extends within the measurement chamber internal volume and is configured to at least one of convey the test signal to the DUT and receive the resultant signal from the DUT;
   an access chamber that defines an access chamber internal volume;
   a measurement chamber door that is configured to selectively isolate the measurement chamber internal volume from the access chamber internal volume;

a transfer assembly that is configured to selectively transfer the substrate through the measurement chamber door and thus between the measurement chamber internal volume and the access chamber internal volume; and an access chamber purging assembly that is configured to selectively direct a heated access chamber dry gas stream in fluid contact with the substrate when the substrate is located within the access chamber internal volume.

6. The probe system of claim 5, wherein the measurement chamber temperature-control assembly is configured to heat an access chamber source gas stream to produce the heated access chamber dry gas stream.

7. The probe system of claim 5, wherein the measurement chamber temperature-control assembly includes:
   a thermal management fluid inlet that is configured to receive a thermal management fluid stream;
   a thermal management fluid outlet that is configured to produce a temperature-controlled thermal management fluid stream;
   an exchange fluid inlet that is configured to receive an exchange fluid stream; and
   an exchange fluid outlet that is configured to produce a heated exchange fluid stream;
   wherein the measurement chamber temperature-control assembly is configured to exchange thermal energy between the thermal management fluid stream and the exchange fluid stream to produce the temperature-controlled thermal management fluid stream and the heated exchange fluid stream, and wherein the measurement chamber temperature-control assembly is configured to cool the substrate within the measurement chamber internal volume with the temperature-controlled thermal management fluid stream.

8. The probe system of claim 7, wherein the probe system further comprises a measurement chamber exhaust conduit that is configured to convey a gas stream from the measurement chamber internal volume and provide the gas stream to the exchange fluid inlet of the measurement chamber temperature-control assembly as the exchange fluid stream.

9. The probe system of claim 8, wherein the probe system further comprises an exchange fluid outlet conduit that is configured to receive the heated exchange fluid stream from the exchange fluid outlet and convey the heated exchange fluid stream to the access chamber purging assembly as the heated access chamber dry gas stream.

10. The probe system of claim 5, wherein the probe system further comprises a measurement chamber exhaust conduit that is configured to convey a gas stream from the measurement chamber internal volume to an access chamber gas conditioner as an access chamber source gas stream.

11. The probe system of claim 10, wherein the access chamber gas conditioner is configured to accept the access chamber source gas stream and to transform the access chamber source gas stream into the heated access chamber dry gas stream by at least one of drying and heating.

12. The probe system of claim 5, further comprising a measurement chamber purging assembly that is configured to direct a measurement chamber dry gas stream into the measurement chamber internal volume and to create a positive pressure differential between the measurement chamber internal volume and the ambient environment during testing of the DUT.

13. A method of testing a device under test (DUT) with a probe system including a measurement chamber, the method comprising:

establishing a low temperature and a dry environment within a measurement chamber internal volume of the measurement chamber by directing a measurement chamber dry gas stream into the measurement chamber internal volume, wherein the establishing includes creating a positive pressure differential between the measurement chamber internal volume and an ambient environment that surrounds the probe system;

placing a substrate with a DUT into the measurement chamber internal volume;

testing the DUT by providing a test signal to the DUT and receiving a resultant signal from the DUT;

removing the substrate from the measurement chamber internal volume; and dry heating the substrate at least partially outside of the measurement chamber internal volume while at least partially isolating the substrate from the ambient environment.

14. The method of claim 13, wherein the establishing includes purging the measurement chamber internal volume with the measurement chamber dry gas stream during the testing.

15. The method of claim 13, wherein the placing includes moving the substrate from an access chamber internal volume of an access chamber of the probe system, through a measurement chamber door of the probe system, and into the measurement chamber internal volume.

16. The method of claim 13, wherein the removing includes moving the substrate from the measurement chamber internal volume, through a measurement chamber door of the probe system, and into an access chamber internal volume of an access chamber of the probe system.

17. The method of claim 13, wherein the dry heating includes selectively directing an access chamber dry gas stream that is warmer than the substrate into fluid contact with the substrate to heat the substrate.

18. The method of claim 13, wherein the dry heating includes heating at least partially concurrently with the removing.

19. The method of claim 13, wherein the substrate is a first substrate of a plurality of substrates, and wherein the method further comprises repeating the placing, the testing, the removing, and the dry heating for each substrate of the plurality of substrates.

20. The method of claim 19, wherein the plurality of substrates includes a second substrate, and wherein the placing, with respect to the second substrate, is at least partially concurrent with the dry heating, with respect to the first substrate.

21. The method of claim 13, wherein the method further comprises establishing, subsequent to the testing, a second temperature within the measurement chamber that is different than the low temperature, and subsequently repeating the placing, the testing, and the removing.

22. The method of claim 21, wherein the substrate is a first substrate of a plurality of substrates, and wherein the method comprises repeating, at the low temperature, the placing, the testing, the removing, and the dry heating for each substrate of the plurality of substrates, and, after all substrates of the plurality of substrates have been tested at the low temperature, further comprises repeating, at the second temperature, the placing, the testing, and the removing for each substrate of the plurality of substrates.

23. The method of claim 13, wherein the method further includes:
   discharging an exchange fluid stream from the measurement chamber internal volume, wherein the exchange fluid stream includes at least a portion of the measurement chamber dry gas stream;
receiving the exchange fluid stream with a measurement chamber temperature-control assembly;
receiving a thermal management fluid stream from a chuck, which extends within the measurement chamber internal volume, with the measurement chamber temperature-control assembly;
cooling the thermal management fluid stream within the measurement chamber temperature-control assembly via thermal exchange between the thermal management fluid stream and the exchange fluid stream, wherein the cooling includes:
(i) generating a temperature-controlled thermal management fluid stream from the thermal management fluid stream; and
(ii) generating a heated exchange fluid stream from the exchange fluid stream;
discharging the temperature-controlled thermal management fluid stream from the measurement chamber temperature-control assembly;
providing the temperature-controlled thermal management fluid stream to the chuck to cool the chuck; and
directing the heated exchange fluid stream into fluid contact with the substrate to dry heat the substrate.

* * * * *